United States Patent [19]

Thorn et al.

[11] 4,018,534
[45] Apr. 19, 1977

[54] AEROSOL AVERAGE-DENSITY DETERMINING SYSTEM

[75] Inventors: Lawrence B. Thorn; David R. Dreitzler, both of Huntsville, Ala.

[73] Assignee: The United States of America as represented by the Secretary of the Army, Washington, D.C.

[22] Filed: May 21, 1975

[21] Appl. No.: 579,657

[52] U.S. Cl. .............................. 356/201; 250/575; 356/207
[51] Int. Cl.² ........................................ G01N 21/22
[58] Field of Search ................. 356/201, 207, 227; 250/575, 227

[56] References Cited

UNITED STATES PATENTS

| | | | |
|---|---|---|---|
| 3,820,897 | 6/1974 | Roess | 356/201 |
| 3,869,208 | 3/1975 | Lorenz | 250/227 |

Primary Examiner—Vincent P. McGraw
Attorney, Agent, or Firm—Nathan Edelberg; Robert P. Gibson; Freddie M. Bush

[57] ABSTRACT

Light shown through a space containing smoke or an aerosol is detected from several paths through the space. The light may be gathered from physically separated optical fibers feeding a common photodetector, or several physically separated, series-connected photodetectors may be used. The total amount of light reaching the photodetector(s) is directly related to the average density of the smoke or aerosol.

1 Claim, 2 Drawing Figures

AEROSOL AVERAGE-DENSITY DETERMINING SYSTEM

DEDICATORY CLAUSE

The invention described herein may be manufactured, used, and licensed by or for the Government for governmental purposes without the payment to use of any royalties thereon.

BACKGROUND OF THE INVENTION

There exist many systems for smoke and/or aerosol detection in closed (or open) spaces. Some such systems employ light sources with photodetectors. Most of these systems are not, however, concerned with average smoke/aerosol density detection, and have a single path for a light beam between its source and a detector. Other systems use reflectors to extend the path length through the space. While these last-mentioned systems do provide some indication of average density, they do it at the expense of complex optical systems, i.e., the various reflectors must be accurately aligned. The instant invention is able to determine smoke/aerosol average density with a simple and straightforward system.

SUMMARY OF THE INVENTION

The invention is an aerosol average-density determining system for some space. A light is shown through the space, and the light from several different paths through the space is detected. The light is detected by a respective photodetector for each path, with the photodetectors being connected in series, or by a single photodetector fed by optical fibers, with a respective fiber for each path. The output of the photodetector(s) is directly related to average aerosol density.

DETAILED DESCRIPTION OF THE INVENTION

Figure 1:
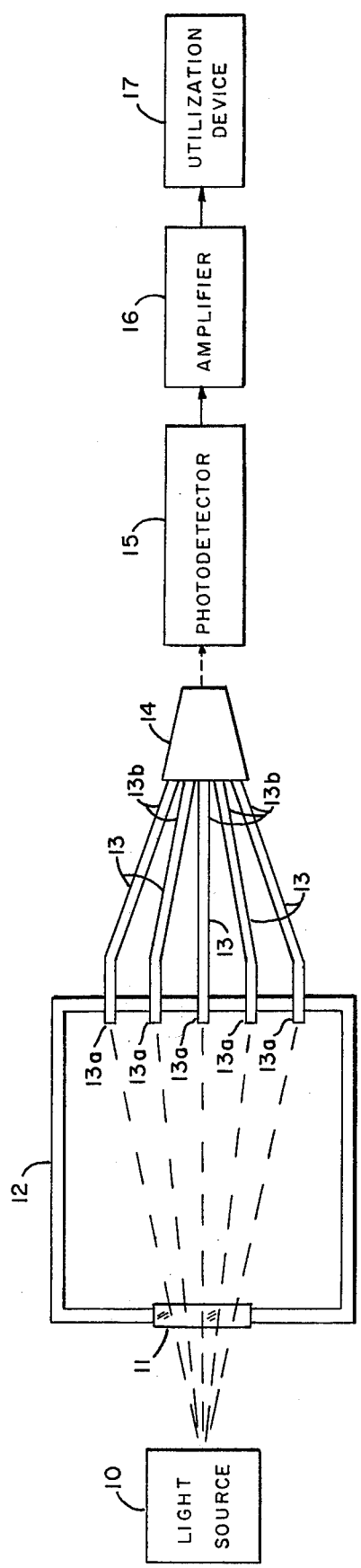
FIG. 1 is a schematic diagram of one embodiment of the invention.

The invention may be best understood by referring to the drawings, in which the embodiment of the invention shown in FIG. 1 includes a light source 10 shining through window 11 on one side of chamber 12. On the opposite side of chamber 12 are optical fibers 13 having ends 13a extending into the interior of chamber 12. Ends 13b of fibers 13 are brought together at reflecting cone 14. The light from fibers 13 is combined in cone 14 and is applied to photodetector 15. The output of 15 is amplified by amplifier 16 and applied to utilization device 17. This device 17 may be a recorder, an alarm, etc.

Figure 2:
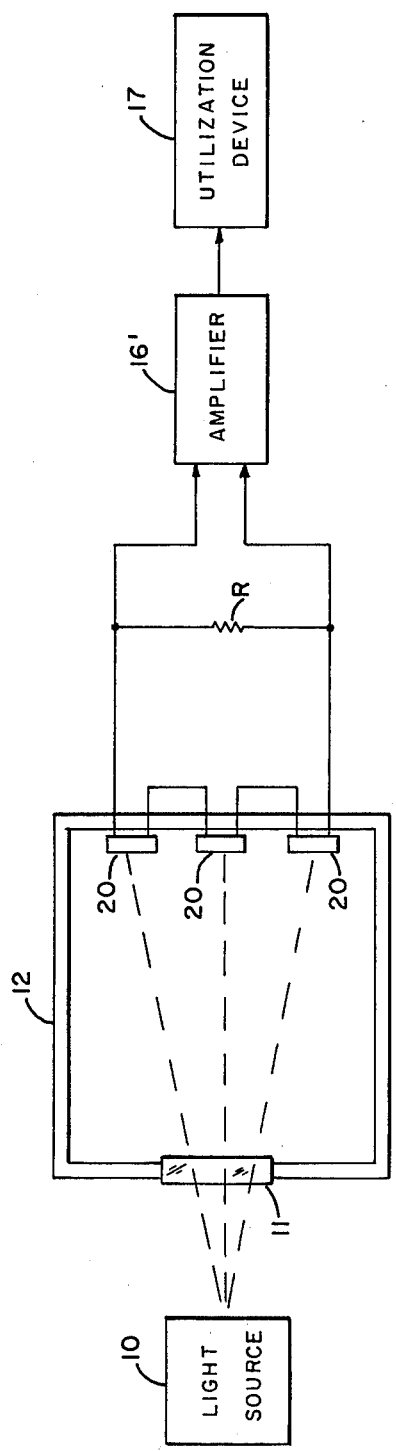
FIG. 2 is a schematic diagram of another embodiment of the invention.

FIG. 2 has some elements equivalent to those of FIG. 1 and corresponding reference numerals are used. Light source 10 of FIG. 2 shines through window 11 of chamber 12 and falls on series-connected photodetectors 20. For photodetectors of a photovoltaic type, resistor R is connected as a load resistor, with the voltage across R being applied to amplifier 16'. The output of 16' is applied to utilization 17.

Operation of the invention should be clear with the drawings in mind. Smoke or aerosol in chamber 12 will diminish the amount of light that will pass along each light path in 12. The sum of the light passing through all of the paths is then directly related to the average density of smoke/aerosol in the chamber. This sum is accomplished by fibers 13, cone 14, detector 15 of FIG. 1, and by detectors 20 and resistor R of FIG. 2.

While a specific embodiment of the invention has been shown and described, obviously other embodiments of the invention may be obvious to ones skilled in the art, without departing from the concepts of the invention. Specifically, although fibers 13 are shown in a line, they might also be in a two-directional array. Moreover, for a photodetector with a sensitive surface of sufficient size, cone 14 may be eliminated. Obviously any light-guiding equivalent of optical fibers 13 might be used. If desired, light source 10 may be chopped, in the usual manner. Source 10 could be in chamber 12 rather than outside. The various photodetectors 15 and 20 may be photoresistive or photovoltaic, as desired. A photoresistive detector in FIG. 2 would obviously require a voltage source in series with resistor R. While the invention has been shown in use with a chamber, obviously it could be used to advantage in any open or closed space.

We claim:

1. An aerosol average density determining system including a single light source for providing light along plural paths through said aerosol; and means for detecting light from said plural paths, said means for detecting includes a respective photosensitive means for each of said paths, said photosensitive means having outputs connected in series.

* * * * *